United States Patent [19]

Anderson et al.

[11] Patent Number: 5,135,736
[45] Date of Patent: Aug. 4, 1992

[54] COVALENTLY-LINKED COMPLEXES AND METHODS FOR ENHANCED CYTOTOXICITY AND IMAGING

[75] Inventors: David C. Anderson, Seattle; A. C. Morgan, Jr., Edmonds; Paul G. Abrams, Seattle, all of Wash.

[73] Assignee: NeoRx Corporation, Seattle, Wash.

[21] Appl. No.: 232,337

[22] Filed: Aug. 15, 1988

[51] Int. Cl.⁵ .............. A61K 39/44; A61K 49/02; A61K 49/04
[52] U.S. Cl. ........................... 424/1.1; 424/9; 424/85.91; 424/94.3; 514/8; 514/12; 514/21; 530/395; 530/391.7; 530/389.7; 530/288.15; 530/388.8; 530/387.1; 530/391.3; 435/188
[58] Field of Search ............ 530/390, 391, 388, 395; 424/1.1, 9, 85.91, 94.3; 514/12, 21, 8; 435/188

[56] References Cited

U.S. PATENT DOCUMENTS

| | | | |
|---|---|---|---|
| 4,046,722 | 9/1977 | Rowland | 530/362 |
| 4,675,382 | 6/1987 | Murphy | 530/350 |
| 4,831,122 | 5/1989 | Buchsbaum et al. | 530/389 |
| 4,859,449 | 8/1989 | Mattes | 424/9 |
| 4,892,827 | 1/1990 | Pastan et al. | 435/193 |
| 4,894,443 | 1/1990 | Greenfield et al. | 530/388 |

FOREIGN PATENT DOCUMENTS 0282057  9/1988  European Pat. Off. .

OTHER PUBLICATIONS

Thorpe et al. (1982) Immunological Rev. 62: 119-158.
Laberboum-Galski et al. (1988) Proc. Natl Acad. S.C. USA 85:1922-1926.
Chandhary et al. (1987) Proc. Natl. Acad. Sci. USA 84:4538-4542.
J. M. Boggs et al., Chem. Abstr. 108:48913a (1987).
N. K. Subbarao et al., Biochemistry 26:2964-72 (1987).
R. P. Parente et al., J. Biol. Chem. 263:4724-30 (1988).
Quay et al., "Conformational Studies of Aqueous Melittin: Thermodynamic Parameters of the Monomer-Tetramer Self-Association Reaction," Biochemistry, 22: 693-700, 1983.
Schubert et al., "Does Dimeric Melittin Occur in Aqueous Solutions?", Biophys. J., 48: 327-9, 1985.
Talbot et al., "Melittin—Phospholipid Interactions: Binding of the Mono- and Tetrameric Form of this Peptide, and Perturbations of the Thermotropic Properties of Bilayers," Toxicon, 20: (No. 1) 199-202, 1982.
Subbarao et al., "pH-Dependent Bilayer Destabilization by an Amphipathic Peptide," Biochemistry, 26: 2960-2972, 1987.
Parente et al., "pH-Dependent Fusions of Phosphatidylcholine Small Vesicles," The Journal of Biological Chemistry, 263: (No. 10) 4724-30, 1988.

Primary Examiner—Christine Nucker
Assistant Examiner—Kay K. Kim
Attorney, Agent, or Firm—Stoel Rives Boley Jones & Grey

[57] ABSTRACT

Covalently-linked complexes (CLCs) for targeting a defined population of cells, comprising a targeting protein or peptide; a cytotoxic agent; and an enhancing moiety, wherein the enhancing moiety is capable of promoting CLC-membrane interaction are disclosed. Methods for using the claimed CLCs to obtain enhanced in vivo cytotoxicity and enhanced in vivo imaging are also described.

13 Claims, 1 Drawing Sheet

COVALENTLY-LINKED COMPLEXES AND METHODS FOR ENHANCED CYTOTOXICITY AND IMAGING

TECHNICAL FIELD

The present invention relates to covalently-linked complexes (CLC) having enhanced diagnostic or therapeutic properties and methods of using these complexes. The CLC of the present invention has three components: (1) a targeting protein or peptide; (2) a cytotoxic agent, such as a radioisotope, a drug or a toxin; and (3) one or more enhancing moieties capable of promoting CLC-target cell membrane interaction.

BACKGROUND OF THE INVENTION

Immunoconjugates consisting of antibody joined to a cytotoxic agent have been used in attempts to achieve selective killing of particular target cells, such as tumor cells. In theory, immunoconjugates or targeting protein conjugates should effect specific cellular cytotoxicity. In practice, however, in vivo administration of immunoconjugates has proven less efficacious than anticipated.

Several disadvantages related to retention, internalization and translocation of immunoconjugates have been identified. For instance, optimal retention of isotope-antibody fragment conjugates within tumor tissue after in vivo administration has not been demonstrated. Additional problems associated with target cell internalization and translocation of immunoconjugates have been recognized, particularly in regards to translocation and internalization of A-chain (derived from plant o r bacterial toxin) immunoconjugates.

Thus, there is a need in the art for improved: (1) retention of targeting protein conjugates (especially antibody fragment conjugates) at target cell plasma membranes; (2) internalization of targeting protein conjugates into target cell endosomic vesicles; and (3) translocation of targeting protein conjugates across target cell endosomic vesicular membranes into the cytoplasm. Enhancement of the interaction of targeting protein conjugates with plasma membranes and/or internal membranes of target cells may improve the cytotoxicity of targeting protein conjugates administered in vivo. The present invention fulfills this need and further provides other related advantages.

SUMMARY OF THE INVENTION

The present invention describes a covalently-linked complex (CLC) for targeting a defined population of cells, comprising a targeting protein or a targeting peptide; a cytotoxic agent; and an enhancing moiety, wherein the enhancing moiety is capable of promoting CLC-membrane interaction.

A method for enhancing in vivo cytotoxicity of a targeting protein conjugate comprising administering to a tumor-bearing patient a therapeutically effective amount of the covalently-linked complex of the present invention is also disclosed.

In addition, a method for enhanced in vivo imaging of a tumor comprising administering to a tumor-bearing patient a diagnostically effective amount of the claimed covalently-linked complex is disclosed.

DETAILED DESCRIPTION OF THE INVENTION

Figure 1:
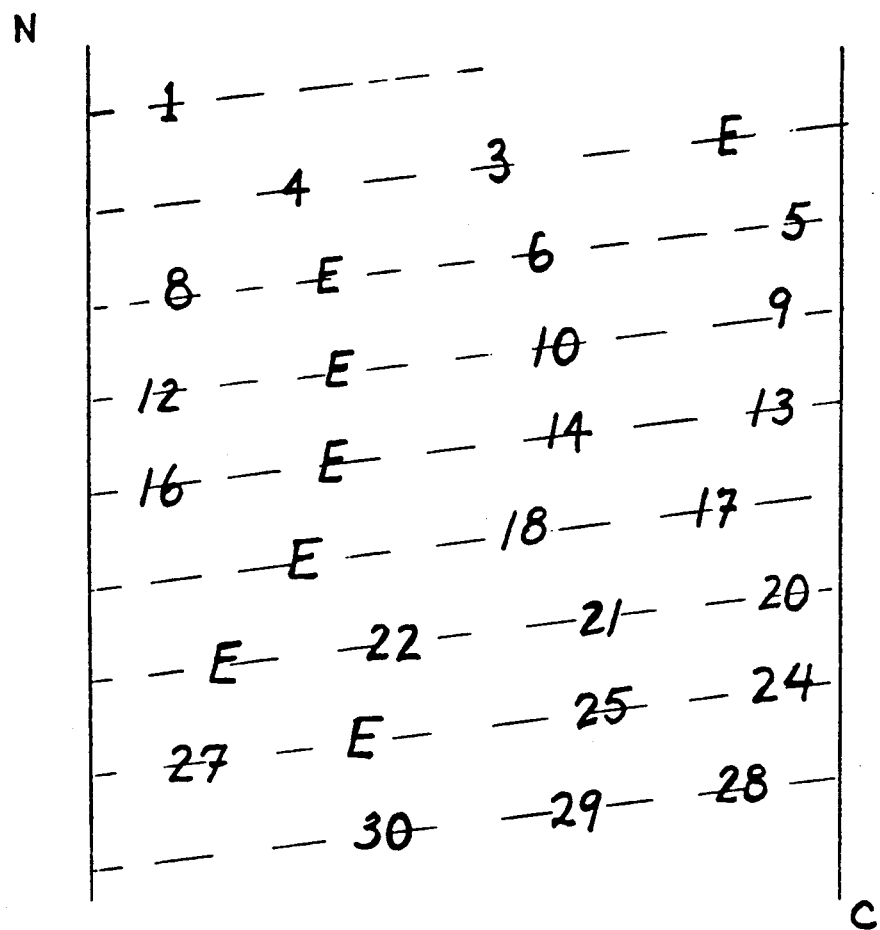
FIG. 1 illustrates a helical net structure representing an advantageous spatial arrangement of amino acids present in a translocating peptide of the present invention.

Prior to setting forth the invention, it may be helpful to set forth definitions of certain terms to be used within the disclosure.

Targeting protein or targeting peptide: A protein or peptide that binds to a defined population of cells. The targeting protein or peptide may bind a receptor, an enzymatic substrate, an antigenic determinant, or other binding site present on the target cell population. Hereinafter, the term "targeting protein" will be inclusive of both targeting proteins and targeting peptides.

Translocating peptide: A peptide capable of insertion into membranes at acidic pH (typically pH 5.0-5.5).

Anchoring peptide: A peptide capable of insertion into membranes at physiological pH (typically pH 6.8-7.5).

Accessory peptide: A peptide or non-peptide molecule that serves as a substrate for target cell enzymes, and promotes membrane retention or translocation of an anchoring and/or translocating peptide.

Fusion protein: A hybrid protein generated by means of recombinant DNA technology. A fusion protein is translated from messenger RNA as one continuous polypeptide chain, with the protein or peptide components joined together by peptide bonds.

Conjugate: A two-component hybrid molecule wherein the components are joined by a covalent chemical linkage.

Targeting protein conjugate: A conjugate wherein one component is antibody (i.e., an immunoconjugate) or, more generally, a targeting protein. Typically, the second component of a targeting protein conjugate is a cytotoxic agent, such as a drug, a toxin or a radionuclide. In contrast to fusion proteins, recombinant DNA methods are not involved in the covalent linkage of targeting protein conjugate components.

Covalently-linked complex (CLC): A three-component complex comprising (1) a targeting protein; (2) a cytotoxic agent; and (3) an enhancing moiety; wherein the three components of the CLC are joined together by covalent bonds.

Enhancing moiety: A moiety capable of promoting membrane interaction. Enhancing moieties of the present invention include translocating peptides, anchoring peptides, accessory peptides and organic membrane intercalators. In addition, an enhancing moiety may be fused to one or more components of a fusion protein. One or more enhancing moieties may be covalently attached to a targeting protein conjugate to form a CLC having enhanced membrane interactive characteristics.

In general, three levels of targeting protein conjugate-membrane interaction have been identified that may be important for optimal in vivo diagnostic or therapeutic efficacy: (1) binding of the conjugate to the target cell plasma membrane; (2) internalization of the conjugate into endosomic vesicles; and (3) translocation of the conjugate from endosomic vesicles into the cytoplasm, which gives a targeting protein conjugate access to cytoplasmic or nuclear target sites. If any one of these targeting protein conjugate-membrane interactive steps becomes rate-limiting, targeting protein conjugate potency may be diminished.

Optimization of the three levels of target cell membrane interaction noted above (i.e., retention, translocation, internalization) may enhance the cytotoxicity of targeting protein conjugates. Different types of targeting protein conjugates (for instance, targeting protein conjugated to either a drug, toxin or radioisotope) may require different levels of targeting protein conjugate-membrane interaction in order to achieve optimal cytotoxicity in vivo.

More specifically, radioisotope-targeting protein conjugates require binding and prolonged retention of the conjugate, either within the tumor or at the tumor cell plasma membrane, for maximal cytotoxic efficacy. Drug-targeting protein conjugates that are active at the plasma membrane may require (1) binding of the targeting protein conjugate at the plasma membrane, and (2) expression of cytolytic activity at the plasma membrane. Drug-targeting protein conjugates that are not active at the target cell plasma membrane additionally require internalization of the drug for cytotoxicity. Drug conjugates of this latter type and toxin-targeting protein conjugates require three levels of membrane interaction for cytotoxicity: (1) binding of the targeting protein conjugate at the plasma membrane; (2) internalization of the conjugate within the target cell; and (3) translocation of the conjugate from endosomic vesicles into the cytoplasm.

The "targeting protein" component of the covalently-linked complex (CLC) of the present invention directs a covalently-attached cytotoxic agent to a target cell population, such as tumor cells. Preferred targeting proteins useful in this regard include antibody and antibody fragments; peptides, such as bombesin, gastrin-releasing peptide, RGD peptide, substance P, neuromedin-B, neuromedin-C, and metenkephalin; and hormones, such as EGF, α- and β-TGF, estradiol, neurotensin, melanocyte stimulating hormone, follicle stimulating hormone, luteinizing hormone, and human growth hormone. Biotin, avidin, proteins corresponding to known cell surface receptors (including low density lipoproteins, transferrin and insulin), fibrinolytic enzymes, and biological response modifiers (including interleukin, interferon, erythropoietin and colony-stimulating factor) are also preferred targeting proteins. Analogs of the above-listed targeting proteins that retain the capacity to bind to a defined target cell population may also be used within the claimed invention. In addition, synthetic targeting proteins and peptides may be designed.

Monoclonal antibodies have precise specificity for a particular epitope present on a target cell population. When a cytotoxic agent, such as a drug, toxin or radioisotope, is conjugated to a monoclonal antibody, increased amounts of the cytotoxic agent may be administered in vivo (as compared to the unconjugated form of the cytotoxic agent), due to the selective targeting properties of the monoclonal antibody component of the conjugate.

Types of cytotoxic agents useful herein include toxins, drugs and radionuclides. Several of the potent toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting protein. However, while elimination of the toxin B chain decreases non-specific cytotoxicity, it also generally leads to decreased potency of the toxin A chain-targeting protein conjugate, as compared to the corresponding holotoxin-targeting protein conjugate.

One possible explanation for the decreased potency of A chain-targeting protein conjugates is that B chain is required for translocation of the A chain across endosomic membranes into the target cell cytoplasm. In the absence of translocation, the targeting protein conjugate remains in the interior of an endosome, and is ultimately transported to a lysosome. Within the lysosome, the targeting protein conjugate is degraded, and thus the A chain cytotoxic agent fails to reach its cytoplasmic target site. The decreased potency associated with toxin A chain-targeting protein conjugates also accompanies the use of ribosomal inactivating protein-targeting protein conjugates. Ribosomal inactivating proteins (RIPs) are naturally occurring protein synthesis inhibitors that lack translocating and cell-binding ability.

Within the present invention, preferred toxins include holotoxins, such as abrin, ricin, modeccin, Pseudomonas exotoxin A, Diphtheria toxin, pertussis toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides.

Preferred drugs suitable for use herein include conventional chemotherapeutics, such as vinblastine, doxorubicin, bleomycin, methotrexate, 5-fluorouracil, 6-thioguanine, cytarabine, cyclophosphamide and cis-platinum, as well as other conventional chemotherapeutics as described in *Cancer: Principles and Practice of Oncology*, 2d ed., V. T. DeVita, Jr., S. Hellman, S. A. Rosenberg, J. B. Lippincott Co., Philadelphia, Pa., 1985, Chapter 14. A particularly preferred drug within the present invention is a trichothecene.

Experimental drugs, such as mercaptopurine, N-methylformamide, 2-amino-1,3,4-thiadiazole, melphalan, hexamethylmelamine, gallium nitrate, 3% thymidine, dichloromethotrexate, mitoguazone, suramin, bromodeoxyuridine, iododeoxyuridine, semustine, 1-(2-chloroethyl)-3-(2,6-dioxo-3-piperidyl)-1-nitrosourea, N,N'-hexamethylene-bis-acetamide, azacitidine, dibromodulcitol, Erwinia asparaginase, ifosfamide, 2-mercaptoethane sulfonate, teniposide, taxol, 3-deazauridine, soluble Baker's antifol, homoharringtonine, cyclocytidine, acivicin, ICRF-187, spiromustine, levamisole, chlorozotocin, aziridinyl benzoquinone, spirogermanium, aclarubicin, pentostatin, PALA, protein conjugates, only plasma membrane interaction is required, but effective cytotoxicity requires prolonged retention of the conjugate at the target membrane.

The present invention discloses compositions and methods that promote interaction(s) of targeting protein conjugates with various target cell membranes. More specifically, biochemical linkage of a targeting protein conjugate and one or more enhancing moieties capable of promoting membrane interaction (or construction of an analogous recombinant fusion protein) results in a "covalently-linked complex" (CLC) having improved membrane interactive properties.

Enhancing moieties useful within the present invention may be subdivided into several categories. The first category of enhancing moieties is designated "translocating peptides," and includes pH-dependent membrane-binding peptides. The second category is designated "anchoring peptides," and includes membrane soluble peptide sequences and analogs thereof. Anchoring peptides are capable of binding to target cell membranes at physiologic pHs. A third category, "accessory peptides," may be used in conjunction with translocating or anchoring peptides to enhance membrane retention and/or translocation. A fourth category of enhancing moieties includes membrane permeation enhancers, designated "organic membrane intercalators," such as fatty acids and analogs thereof, bile salts, membrane anesthetics, phospholipids, medium chain glycerides and fusidic acid.

In an alternative embodiment, one or more enhancing moieties may be included in a fusion protein. For generation of a fusion protein that contains an enhancing moiety, a first DNA sequence (corresponding to a targeting protein, a cytotoxic agent or an enhancing moiety) is joined at the DNA level through recombinant DNA technology to a similar or dissimilar second (third, fourth, etc.) DNA sequence. The resultant fused DNA carboplatin, amsacrine, caracemide, iproplatin, misonidazole, dihydro-5-azacytidine, 4'-decoxy-doxorubicin, menogaril, triciribine phosphate, fazarabine, tiazofurin, teroxirone, ethiofos, N-(2-hydroxyethyl)-2-nitro-1H-imidazole-1-acetamide, mitroxantrone, acodazole, amonafide, fludarabine phosphate, pibenzimol, didemnin B, merbarone, dihydrolenperone, flavone-8-acetic acid, oxantrazole, ipomeanol, trimetrexate, deoxyspergualin, echinomycin, and dideoxycytidine (see *NCI Investigational Drugs, Pharmaceutical Data* 1987, NIH Publication No. 88-2141, Revised November 1987) are also preferred.

Radionuclides useful within the present invention include gamma-emitters, positron-emitters, Auger electron-emitters, X-ray emitters and fluorescenceemitters, with beta- or alpha-emitters preferred for therapeutic use. Radionuclides are well-known in the art and include $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{76}$Br, $^{77}$Br, $^{99m}$Tc, $^{11}$C, $^{13}$N, $^{15}$O and $^{18}$F. Preferred therapeutic radionuclides include $^{188}$Re, $^{186}$Re, $^{203}$Pb, $^{212}$Pb, $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au and $^{199}$Ag.

As noted above, with toxin-targeting protein conjugates, the limiting membrane interactive events appear to be the rate of internalization and the rate of translocation. With respect to drug-targeting protein conjugates that are not active at the plasma membrane, internalization of the targeting protein conjugate is required, with release of the drug from endosomic vesicles before the conjugate reaches the lysosome (i.e., is degraded). With drug-targeting protein conjugates that are active at the plasma membrane, internalization is not required, but a strong, prolonged interaction of the drug conjugate at the plasma membrane is important for cytotoxic efficacy. For radionuclide-targeting sequences are transcribed and translated into a hybrid fusion protein. When an enhancing moiety is incorporated into a fusion protein, the resultant fusion protein possesses improved membrane interactive properties.

In general, according to the present invention, the targeting protein component of a covalently-linked complex recognizes a binding site at the target cell membrane surface. A primary target cell interaction mediated by the targeting protein component of the CLC is followed by a secondary interaction of the enhancing moiety component with the plasma membrane. This secondary interaction between enhancing moiety and membrane stabilizes the targeting protein at the membrane surface. In instances where an antibody (or antibody fragment) is the targeting protein, interaction of enhancing moiety and target cell membrane may also increase the affinity of an antibody for its antigen.

Translocating Peptides

The first category of enhancing moiety consists of translocating peptides, which exhibit pH-dependent membrane binding. When a translocating peptide assumes a helical conformation at an acidic pH, the translocating peptide acquires the property of amphiphilicity, e.g., it has both hydrophobic and hydrophilic interfaces. More specifically, within a pH range of approximately 5.0–5.5, a translocating peptide forms an alpha-helical, amphiphilic structure that facilitates insertion of the translocating peptide into a target membrane. An alphahelix-inducing acidic pH environment may be found, for example, in the low pH environment present within cellular endosomes.

In aqueous solution at physiological pH, a translocating peptide is unfolded (due to strong charge repulsion among charged amino acid side chains) and is unable to interact with membranes. Within the present invention, it may be advantageous to position amino acid residues within the translocating peptide sequence so that charged amino acid side chains will stack one above the other when the peptide folds into an amphiphilic alpha helix at reduced pH. FIG. 1 represents a helical net display that illustrates an advantageous spatial arrangement of the charged side chains.

Charged amino acids capable of stacking within a translocating peptide sequence include glutamate, aspartate and histidine. A preferred pH-dependent membrane-binding translocating peptide includes a high percentage of helix-forming residues, such as glutamate, methionine, alanine and leucine. In addition, a preferred translocating peptide sequence includes ionizable residues having pKa's within the range of pH 5–7, so that a sufficient uncharged membrane-binding domain will be present within the peptide at pH 5 to allow insertion into the target cell membrane.

A particularly preferred pH-dependent membrane-binding translocating peptide in this regard is aa1-aa2-aa3-EAALA(EALA)$_4$-EALEALAA-amide, which represents a modification of the peptide sequence of Subbarao et al. (*Biochemistry* 26: 2964, 1987). Within this peptide sequence, the first amino acid residue (aa1) is preferably a unique residue, such as cysteine or lysine, that facilitates chemical conjugation of the translocating peptide to a targeting protein conjugate. Amino acid residues 2–3 may be selected to modulate the affinity of the translocating peptide for different membranes. For instance, if both residues 2 and 3 are lys or arg, the translocating peptide will have the capacity to bind to membranes or patches of lipids having a negative surface charge. If residues 2–3 are neutral amino acids, the translocating peptide will insert into neutral membranes.

Yet other preferred translocating peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary translocating peptides may be modified through attachment of substituents that enhance the alpha-helical character of the translocating peptide at acidic pH.

An example of a modified peptide having translocating activity at acidic pH is fully succinylated melittin. In this example, a peptide (melittin) that normally binds to membranes at physiological pH is converted to a pH-dependent translocating peptide through succinylation of lysines. Upon succinylation, the peptide displays an amphipathic character only at acidic pHs.

Within the present invention, translocating peptides may be designed and synthesized to provide enhanced membrane interaction(s). For instance, translocating peptides conforming to the helical net structure depicted in FIG. 1 may be generated. More specifically, in a translocating peptide designed according to FIG. 1, stacked glutamates may occupy positions in the helical net that are designated as "E"; the remaining amino acid residues may consist (entirely or predominantly) of strong neutral helix formers, such as methionine, alanine or leucine.

Insertion of a translocating peptide into a target cell membrane may be enhanced through stabilization of the amphiphilic alpha helix. Helix stabilization may be achieved: (1) by adding repeating "EALA" units to form a longer peptide; (2) by placing an amide at the C-terminus of the peptide, in order to counteract the helical dipole; (3) by polymerizing the peptide; (4) by substituting a neutral helix-former for one or more of the stacked glutamates; or (5) by attaching the peptide to a targeting protein conjugate through use of a longer crosslinking agent, in order to provide sufficient distance between the translocating peptide and the targeting protein conjugate to allow the peptide to contact and interact with the target cell membrane.

The amino acid sequence of a pH-dependent, membrane-binding translocating peptide of the claimed invention may be selected to include all L-amino acids or all D-amino acids having a side chain pKa from 5.0 to 9.0. D-amino acids may be advantageously used to form non-proteolyzable peptides, because the D-amino acids are not metabolized within the cell. Further, the translocating peptides of the present invention may include a combination of L- and D-amino acids, wherein D-amino acids are substituted for L-amino acids on either side of a proteolytic cleavage site. Yet another preferred noncleavable translocating peptide incorporates peptide bond analogs that are not susceptible to proteolytic cleavage by cellular enzymes.

The pH-dependent, membrane-binding translocating peptides of the present invention may be attached singly or may be polymerized. Chemical linkage of one or more translocating peptides (single, or polymerized) may be accomplished either: (a) by direct attachment of a translocating peptide to a targeting protein conjugate; (b) by disulfide, thioether, reduced or non-reduced Schiff base or peptide bond formation; or (c) by use of a peptide spacer. Preferred peptide spacers in this regard correspond to two or more amino acid residues that allow the translocating peptide to assume an alpha-helical conformation independent of its interaction with the targeting protein conjugate, and may allow sufficient distance for translocating peptide access to the cell surface from the peptide attachment site on the targeting protein.

Polymerization of translocating peptides may be accomplished by placing a cysteine residue at each end of a translocating peptide, followed by oxidation using dissolved oxygen or other mild oxidizing agent, such as oxidized glutathione. The average length of the polymerized translocating peptide may be controlled by varying the polymerization reaction conditions.

Mere membrane intercalation of a translocating peptide may be sufficient for translocation of the peptide across endosomic membranes. However, translocation may be improved by attaching to the translocating peptide moiety a substrate for intracellular enzymes (i.e., an accessory peptide, to be discussed in more detail in a following section). It is preferred that an accessory peptide be attached to a portion(s) of the translocating peptide that protrudes through the endosomic membrane to the cytoplasmic face.

Covalent linkage of an enhancing moiety and a targeting protein conjugate (forming a CLC) may provide enhanced retention of the conjugate (complex) at a target cell plasma membrane upon in vivo administration. In addition, a covalently-linked complex may exhibit more rapid and efficient internalization rates than the corresponding two-component targeting protein conjugate, due to secondary interaction(s) of the enhancing moiety with the plasma membrane. Inclusion of both anchoring and translocating peptides within a CLC may further facilitate initial binding and enhanced translocation of the CLC across endosomic membranes into the target cell cytoplasm.

Anchoring peptides

A second category of enhancing moiety suitable for use within the present invention consists of anchoring peptides. Typically, anchoring peptides contain membrane soluble peptide sequences which are highly apolar and characteristically form alpha helices when inserted into a membrane. When incorporated into a CLC, membrane insertion of the anchoring peptide component may help to secure the targeting protein conjugate component to a target cell membrane, and may further promote internalization of the targeting protein conjugate/CLC.

A model for anchoring peptide interaction with a plasma membrane is the opiate form of beta endorphin. Beta endorphin has one region that is responsible for receptor binding, and another region which can assume an amphiphilic helix (anchoring portion). The amphiphilic helix of beta endorphin is believed to be responsible for an initial membrane interaction, which is followed by diffusion of the hormone through the cell membrane. Diffusion through the membrane allows the receptor-binding region of the molecule to find its appropriate receptor (binding site). In theory, the reverse process may also occur —— the receptor binding portion (targeting portion) of beta endorphin interacts with its receptor, followed by alpha-helix formation and membrane insertion of the anchoring portion of the molecule.

Anchoring peptides suitable for use within the present invention may be (i) chemically synthesized; (ii) made by recombinant DNA technology; or (iii) isolated from viral fusion proteins or other proteins. Viral fusion peptides, such as those described by Gallaher (*Cell.* 50: 327-28, 1987), are exemplary of anchoring peptides of the claimed invention. Preferred viral fusion peptide sequences in this regard may be derived from viral proteins of measles virus, respiratory syncytial virus, Sendai virus, murine mammary tumor virus, human or simian immunodeficiency virus, visna virus, or simian retrovirus. In addition, analogs of viral fusion peptides that retain the capacity to embed within a membrane may be suitable for use within the claimed invention.

AVGAIGAMFLGFLGAAGSTMGAASL represents yet another preferred anchoring peptide sequence that may be incorporated into a covalently-linked complex according to the present invention. An anchoring peptide sequence that includes one or more internal repeats of the sequence "-FLG-" or "-FLA-" or combinations thereof may also be preferred. For some therapeutic applications, the addition of one or more negatively charged residues to the anchoring peptide may be preferred. The additional negatively charged residues may decrease levels of non-specific binding mediated by the peptide domain of the CLC.

In a preferred embodiment, the anchoring peptide sequence includes an N terminal aa1-aa2-aa3 sequence, which is defined in the same manner as "aa1-aa2-aa3" of the pH-dependent, membrane-binding translocating peptides, as described above. In addition, variable length peptide spacers may be added to either terminus of the anchoring peptide sequence. The remainder of the anchoring peptide sequence includes amino acid residues capable of fusing with membranes or lipid bilayers.

In another preferred embodiment of the present invention, an anchoring peptide may be attached to the targeting protein conjugate component of a CLC by means of variable length crosslinking agents. In certain instances, longer crosslinker spacer arms between the enhancing moiety and the targeting protein conjugate are preferred. The span of a longer crosslinking agent permits an anchoring peptide to reach from the binding site of the targeting protein component to the target cell membrane.

In addition, aa2 and aa3 of an anchoring peptide sequence may be substituted with a peptide spacer consisting of 1-40 amino acids. The entire anchoring peptide plus spacer may be produced chemically in one synthetic reaction. In a preferred embodiment, the spacer does not assume a beta sheet or helical shape, and may be retained in an extended conformation at physiological pH by charge repulsion.

A preferred spacer in this regard is CDNDNDDNDDGGG. Alternatively, a preferred peptide spacer would include predominantly polar (charged or uncharged) residues to aid solubility and, for spacers having charged residues, only like charges. The sequence CRQRQRRQRRGGG is exemplary of a positively charged spacer. The peptide spacers of the present invention typically have a unique N-terminal residue (such as cys, lys, asp, or glu) useful for crosslinking to a targeting protein. The insertion of a peptide spacer provides greater distance between the targeting protein binding site and the anchoring peptide, thereby increasing the probability that the anchoring peptide will reach the target cell membrane and insert. For instance, a 10-mer peptide spacer, conformationally decoupled from a helix-forming anchoring peptide by insertion of three glycine residues, would span approximately 30-40 Å in an extended conformation. This type of peptide spacer may also be advantageously used with translocating peptides of the present invention. Alternatively, polymeric forms of anchoring peptides may be used to span the distance from a targeting protein binding site to the target membrane.

In instances where an anchoring peptide has a propensity for non-specific insertion into non-target cell membranes, it may be desirable to decrease the probability of membrane insertion of the anchoring peptide. Anchoring peptide insertion into a membrane could be made less probable (1) by shortening the anchoring peptide; (2) by including weaker neutral helix formers in non-glutamate positions within the peptide sequence (see FIG. 1); (3) by substituting aspartate for glutamate within the anchoring peptide sequence; (4) by synthesizing an anchoring peptide with a C terminal carboxylate group; or (5) by incorporating into the peptide sequence uncharged amino acids that are slightly more hydrophilic than residues of a strongly translocating/anchoring peptide. By implementing such peptide modifications, anchoring peptide dissolution in membranes would be predicted to occur only upon primary interaction of the targeting protein component with its binding site.

In one preferred embodiment, a virus-derived anchoring peptide sequence is covalently attached to a targeting protein conjugate, forming a covalently-linked complex. Antibody fragments, as well as intact antibody molecules, are preferred targeting proteins for anchoring peptide attachment.

Upon in vivo administration of a CLC, a primary interaction of the targeting protein component with its binding site is followed by a secondary interaction of the anchoring peptide component with the target cell plasma membrane. The anchoring peptide component of the CLC is solubilized within the membrane, thereby anchoring the targeting protein conjugate component into the target cell membrane. The anchoring peptide component may also act to enhance translocation of the CLC into the target cell.

Accessory peptides

A third category of enhancing moiety, the "accessory peptides," may be advantageously attached to the carboxy terminus of a translocating or anchoring peptide. An accessory peptide of the present invention may contain one or more amino acid residues. In one embodiment, an accessory peptide may provide a substrate for cellular phosphorylation (for instance, the accessory peptide may contain a tyrosine residue).

To exemplify the use of an accessory peptide within the claimed invention, a phosphorylatable accessory peptide is first covalently attached to the C-terminus of an anchoring peptide and then incorporated into a covalently-linked complex. The anchoring peptide component of the CLC intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the CLC into the membrane. Further, the accessory peptide may enhance the translocation of the CLC into the cell cytoplasm.

Preferred accessory peptides in this regard include kinase-substrate accessory peptides that incorporate serine. A kinase-substrate accessory peptide may be particularly advantageous for enhancement of CLC cytotoxicity of tumor target cells, which have increased levels of protein kinase activity for serines or tyrosines. Increased levels of kinase activity within tumor cells may be attributed to the presence of oncogene products, such as H-ras, on the cytoplasmic side of tumor cell plasma membranes.

Suitable accessory peptides also include peptides that are kinase substrates and peptides that possess a single positive charge. The latter type of accessory peptide may form an ion pair with a "glutamate-like" residue of an attached or closely adjacent translocating peptide. In this regard, it may be desirable to replace an accessory peptide lysine and/or arginine residue(s) with histidine, in order to facilitate movement of a more neutral peptide through a target membrane at acidic pH.

Particularly preferred accessory peptides may be derived from the following proteins and include the indicated amino acid sequences:

| Peptide Source | Sequence |
| --- | --- |
| EGF receptor | DVVDADEYLIPQ |
| EGF fragment | CMHIESLDSYTC |
| Kemptide | RGYALG or RGYSLG |
| Glycogen synthetase | PLSRTLSVAA |
| Transferrin receptor | FSLAR |
| H1 histone | ASGSFKL |
| Casein kinase II substrate | AAAAAASEEE or AAAAAASDDD |
| Insulin receptor auto-phosphorylation substrate | DIYETDYYR |

Other accessory peptides may be advantageously connected to hydrophobic, membrane-soluble anchoring peptides. These accessory peptides (or accessory compounds) may bind to, or be the substrate of, a cellular cytoplasmic protein or enzyme. Preferred accessory peptides in this regard include the following:

| Compound | Structure | Reaction |
| --- | --- | --- |
| Aspartate protease inhibitor | VLPFFVL (both D-leu) | Bind protease |
| Vitamin K-dependent carboxylating enzyme substrate | FALEEI, FALEEL or FALEEV | Carboxylation of glutamates to form gamma-carboxy glutamate |
| Glycerol | | Phosphorylation |
| Pyridoxal | | Phosphorylation |
| Tetrahydrofolate | | Bind folate-requiring enzymes |
| Pantothenic acid | | Bind co-enzyme A synthesizing enzymes |
| Thiamine | | Bind synthetic enzymes for thiamine pyrophosphate |

Organic membrane intercalators

The fourth class of enhancing moiety that may be used to enhance retention of a targeting protein conjugate at cell surfaces includes organic membrane intercalators. Organic membrane intercalators include compounds having high lipophilicity, such as fatty acids and fatty acid analogs, bile acids, membrane anesthetics, phospholipids and glycolipids. This class of enhancing moiety provides improved cell surface retention that is particularly desirable, for instance, with radioisotopic-targeting protein conjugates.

Long-chain fatty acids may be attached to targeting protein conjugates by first modifying fatty acid carboxyl groups to form active esters. The active ester form of the fatty acid may subsequently be conjugated to targeting protein lysines or sulfhydryl groups.

If trans-unsaturated fatty acids are used, it is preferred that the double bond be situated near the middle of the fatty acid molecule. Exemplary trans-unsaturated fatty acids in this regard include trans-vaccenic acid and elaidic acid. Long-chain hydrocarbons that may be hydrolyzed to produce carboxylates, phosphonates or phosphates are also preferred organic membrane intercalators within the present invention.

As an example, the lipophilicity of an antibody Fab-conjugate, which can readily diffuse into tumors, may be modulated through the covalent attachment of long-chain fatty acids or fatty acid analogs. The degree of lipophilicity of the fatty acid-targeting protein conjugate (CLC) may be modified by altering the degree of derivitization of the targeting protein conjugate or the chain length of the attached fatty acid. For intravenous administration, CLCs containing fatty acid-targeting protein conjugate preferably remain soluble in aqueous buffer. Alternatively, fatty acid-containing CLCs may require the presence of low levels of detergent to maintain solubility consistent with pharmaceutical administration.

Long-chain fatty acids are readily metabolizable and thus, for some therapeutic applications, it may be preferable to use a non-metabolizable fatty acid analog for covalent attachment to a targeting protein conjugate. A preferred non-metabolizable fatty acid analog in this regard is myristic acid.

Bile salts may also promote transmembrane movement. More particularly, hydrophobic bile salts, such as ursodeoxycholic acid and chenodeoxycholic acid, may be used to facilitate drug absorption (G. S. Gordon et al., Proc. Natl. Acad. Sci. 82: 7419-23, 1985). Other suitable organic membrane intercalators within the present invention include fusidic acid and medium chain glycerides (K. Higaki et al., Pharm. Res. 5: 309-12, 1988). Medium chain glycerides may be conjugated to a targeting protein through succinylation of a free hydroxyl.

Membrane anesthetics (such as lidocaine and its analogs) and phospholipids (such as phosphatidyl inositol and its analogs) are also preferred organic membrane intercalators within the claimed invention.

In one embodiment of the claimed invention, a fatty acid-targeting protein conjugate CLC first binds to its binding site at the plasma membrane. The initial targeting protein-binding site interaction is followed by a secondary interaction of one or more attached fatty acid side chains with membrane lipids. In the case of a monovalent Fab fragment targeting protein, fatty acid modification may produce an Fab fragment CLC component that has increased binding affinity and prolonged retention on the plasma membrane of the target cell.

Fusion proteins

A DNA sequence corresponding to one or more enhancing moieties selected from the four classes discussed above may be fused to another DNA sequence (corresponding to a targeting protein, a cytotoxic agent and/or an enhancing moiety) to form a fusion protein. Exemplary fusion proteins of the present invention may incorporate: (1) a targeting protein (or portion thereof) and a translocating or anchoring peptide; or (2) the enzymatically active portion of a holotoxin molecule fused to a translocating peptide and an anchoring peptide. In the latter case, the fused protein (for instance, an A chain-translocating peptide-anchoring peptide fusion protein) may be covalently linked to a targeting protein by a variety of methods, as described previously, in order to form a covalently-linked complex of the claimed invention.

More specifically, a recombinant DNA fusion sequence represented by "toxin-spacer-translocating peptide-spacer-anchoring peptide" may be cloned and expressed according to standard procedures. Briefly, the recombinant DNA fusion sequence is inserted in vitro into an expression vector capable of replication in a particular host microorganism. Typically, the expression vector is derived from a plasmid or a virus. See Old and Primrose, *Principals of Gene Manipulation*, 2d ed., University of California Press, 1981, pp. 104-17; PCT Patent Application Publication No. WO 86/00528; U.S. Pat. Nos. 4,599,311 and 4,704,362; and British Patent No. GB 2,119,804.

An expression vector within the present invention contains "expression signals," i.e., DNA sequences, such as promoters or operators, that are required for transcription of fusion DNA sequences into messenger RNA, which is then translated into the fusion protein. The expression signals must be matched (compatible) with the intended host cell. In addition, the fusion ENA sequence is operably linked to these expression signals by appropriate insertion of fusion protein DNA into the expression vector (i.e., the first codon of the fusion DNA sequence is in the same reading frame as an initiation codon).

A number of expression vector/host cell systems have been developed in the art, and include expression vectors suitable for transforming *Escherichia coli* (Old and Primrose, supra, pp. 32-35 and 46-47), *Bacillus subtilis* (Old and Primrose, pp. 51-53), or yeast (Old and Primrose, pp. 62-68). In addition, "shuttle vectors," which are expression vectors that may be transferred between different host microorganisms, have been described by Storms et al., *J. Bacteriol.* 140: 73-82, 1979; and Blanc et al., *Molec. Gen. Genet.* 176: 335-42, 1979. For instance, shuttle vectors with the capacity to replicate in both *E. coli* and *B. subtilis* are known (Old and Primrose, p. 53). Vectors derived from bacteriophages, such as M13 phage, have also proven useful for cloning foreign genes (Old and Primrose, Chapter 5). Standard procedures may be used to insert a recombinant DNA fusion sequence into a suitable expression vector (e.g., homopolymeric tailing, blunt-end ligation, or by linker molecules) (Old and Primrose, p. 92).

Many suitable methods are known for inserting the recombinant DNA fusion sequence/expression vector into a microbial host, in order to generate a recombinant microorganism which expresses the desired recombinant fusion polypeptide. Microorganisms which are suitable as host cells within the present invention include, but are not limited to, prokaryotes, such as gram-negative and gram-positive bacteria, and eukaryotes, such as yeast or mammalian cell lines. Preferred host cells in this regard include *Escherichia coli* and *Saccharomyces cerevisiae*.

Upon transformation of appropriate recipient host cells with a recombinant fusion protein-expression vector, transformants are screened using conventional procedures. Transformant screening techniques will vary according to the particular gene and vector/host system employed.

Selected transformed host cells are cultured in a suitable growth medium under conditions conducive to the production of the desired fusion protein. If the fusion protein is secreted by the host cell, it may be isolated from the culture medium by conventional protein purification techniques. If the desired fusion protein is intracellular, the transformed, cultured cells are collected and then lysed through either mechanical methods (e.g., sonication, homogenization, freeze-thawing, nitrogen compression-decompression, etc.); chemical methods (e.g., treatment with detergents such as sodium dodecyl sulfate, sulfate, guanidine HCl or NP-40); or enzymatic methods (i.e., lysozyme) or combinations thereof. The desired fusion protein may then be purified from the cellular lysate.

In instances where the fusion protein does not incorporate a targeting protein component, the fusion protein will be chemically linked to a targeting protein, according to methods previously discussed.

Preferred fusion proteins within the present invention include: (1) targeting protein: enhancing moiety fusion proteins; (2) targeting protein: drug carrier: enhancing moiety fusion proteins; (3) targeting protein: toxin enzymatic domain: enhancing moiety fusion proteins; (4) toxin enzymatic domain: enhancing moiety fusion proteins; (5) translocating-anchoring peptide fusion proteins; and (6) enhancing moiety-enhancing moiety fusion proteins.

In summary, formation of a covalently-linked complex (i.e., one or more enhancing moieties covalently attached to a targeting protein conjugate) allows increased retention of the targeting protein conjugate component of the complex at the plasma membrane of a target cell. Attaching combinations of enhancing moieties to a targeting protein conjugate may further enhance membrane retention, rapid and efficient internalization of the CLC, and/or translocation across endosomic membranes into the target cell cytoplasm.

To summarize the examples that follow, Example I discloses preparation of a translocating peptidetargeting protein conjugate CLC. Example II describes preparation of a radionuclide-targeting protein-anchoring peptide CLC. Preparation of an organic membrane intercalator-targeting protein conjugate CLC is presented in Example III: preparation of a fusion protein (toxinenhancing moiety)-targeting protein CLC is disclosed in Example IV. Example V describes preparation of an accessory peptide-enhancing moiety-targeting protein conjugate CLC. Example VI presents in vitro and in vivo assessment of retention and translocation of CLCs.

The following examples are offered by way of illustration, and not by way of limitation.

EXAMPLE I

Preparation of a Translocating Peptide-Targeting Protein Conjugate CLC

The translocating peptide KGEAALA(EALA)-$_4$EALEALAA-amide is synthesized using tea-bag methodology and solid phase peptide synthesis procedures described by Merrifield et al. (*Biochemistry* 21: 5020-31, 1982) and Houghten (*Proc. Natl. Acad. Sci. (USA)* 82: 5131-35, 1985) or using a commercially available automated synthesizer, such as the Applied Biosystems 430 A peptide synthesizer. The peptide-amide is deprotected in 45% trifluoroacetic acid-51% methylene chloride-2% ethanedithiol-2% anisole for 20 min, and cleaved from the 4-methylbenzhydrylamine resin using the Tam-Merrifield low-high HF procedure (J. P. Tam et al., *J. Am. Chem. Soc.* 105: 6442-55, 1983). The peptide is then extracted from the resin using 0.1 M ammonium acetate buffer, pH 8, and is lyophilized. The crude translocating peptide is purified using reverse phase HPLC on a Vydac C-4 analytical column (The Separations Group, Hesperia, Calif.), and a linear gradient of 0.5–1.0%/min from 100% acetonitrile + 0.1% v/v trifluoroacetate to 100% acetonitrile + 0.1% trifluoroacetate. The HPLC-purified peptide is analyzed by amino acid analysis (R. L. Heinriksen and S. C. Meredith, *Anal. Biochem.* 160: 65–74, 1984) after gas phase hydrolysis (N. M. Meltzer et al., *Anal. Biochem.* 160: 356–61, 1987). The sequence of the purified translocating peptide may be confirmed by Edman degradation on a commercially available sequencer (R. M. Hewick et al., *J. Biol. Chem.* 15: 7990–8005, 1981).

The purified translocating peptide is conjugated to a heterobifunctional crosslinking reagent, such as succinimidyl 4-(N-maleimido-methyl)cyclohexane-1-carboxylate (SMCC) through its amino terminus. Briefly, the peptide is dissolved in 0.1 M borate buffer, pH 7–9, and the crosslinker, which is dissolved in buffer with as much DMSO as necessary for solubility, is added in equimolar amounts. The peptide-SMCC mixture is reacted for approximately 30 min at room temperature, and the derivatized product is separated using PD-10 gel filtration. The SMCC-derivatized translocating peptide is then combined at a 5:1 ratio with an A chain cytotoxic agent (such as ricin A chain) that has been prereduced with dithiothreitol (DTT) and separated from B chain by reactive blue 2 {(1-amino-4[[4-[[4-chloro-6-[[3(or4)-sulfophenyl]amino]-1,3,5-triazin-2-yl]amino]-3-sulfophenyl]amino]-9,10-dihydro-9,10-dioxo-2-anthracenesulfonic acid)}-sepharose chromatography. The reduced ricin A chain reacts with the maleimide group of the SMCC-derivatized peptide, forming a thioether bond; unreacted derivitized peptide is quickly removed by gel filtration.

The translocating peptide-modified ricin A chain is reacted with iminothiolane to generate further thiol groups, which are then used to create a disulfide bond with DTT (50mM)-treated antibody. The translocating peptide-ricin A chain-antibody CLC is separated from unreacted ricin A chain-translocating peptide by gel filtration on an HPLC TSK 3000 column (BioRad, Richmond, Calif.) using a flow rate of 0.5 ml/min in phosphate-buffered saline (PBS), 0.1 M, pH 7.2.

EXAMPLE II

Preparation of a Radionuclide-Targeting Protein-Anchoring Peptide CLC

A. Chelation and Radiolabeling of a Targeting Protein Prior to Peptide Conjugation Anchoring peptide AVGAIGAMFLGFLGAAGSTMGAASL is chemically synthesized according to the methodology described in Example I. Purified anchoring peptide is conjugated to sulfo-SMCC, a water-soluble heterobifunctional crosslinking reagent, using a modification of the procedure described in Example I (reducing the organic solvent).

Monoclonal antibody NR-CO-02 is prelabeled with $^{188}$Re-MAG$_2$-GABA. Briefly, $^{188}ReO_4^-$ tetrabutylammonium+, obtained from a $^{188}$W/$^{188}$Re generator, is loaded onto a $C_{18}$ reverse phase cartridge (Ultrasphere 5 micron, 1.5 ml/min flow), washed with water to remove nitrates, dried and eluted with ethanol onto strong cation exchange cartridges equilibrated with $Li^+$. The $Li^+$ salt of $ReO_4^-$ elutes directly and is dried under $N_2$ at 75° C. A stannous citrate solution is added, followed by the addition of 2,3,5,6-tetrafluorophenyl S-ethoxyethylthioacetylglycyl glycyl-gamma-aminobutyrate (MAG$_2$-GABA) dissolved in isopropanol. The reaction mixture is incubated at 75° C. for 30 min, with formation of a $^{188}$Re-$N_2S_2$-TFP active ester complex. The $^{188}$Re$N_2S_2$-TFP active ester complex is purified on cartridges of the cation exchange resin, then on $C_{18}$ reverse phase cartridges. More specifically, the ester is loaded, washed with water and water-ethanol, dried under low vacuum, and eluted with ethanol. The resultant solution is dried under blowing $N_2$ at 75° C., and monoclonal antibody in 0.2 M sodium cartonate buffer, pH 9.5, is added. After 15 min, the labeling reaction is terminated by the addition of lysine, which reacts with unreacted active ester. The monoclonal antibody-$^{188}$Re-MAG$_2$-GABA conjugate is purified by gel filtration prior to attachment of an anchoring peptide or anchoring peptide-spacer peptide.

Sulfo-SMCC-derivatized anchoring peptide is reacted with free sulfhydryl groups generated on the $^{188}$Re-MAG$_2$-GABA-monoclonal antibody by reduction with 50 mM DTT. Unbound derivatized anchoring peptide is removed by gel filtration.

Alternatively, a monoclonal antibody-anchoring peptide conjugate may be post-labeled with $^{188}$Re. Briefly, monoclonal antibody is reacted with unlabeled $N_2S_2$-TFP active ester, in a manner analogous to the procedure described for prelabeling with $^{188}$Re-MAG$_2$-GABA. The monoclonal antibody-MAG$_2$-GABA molecule is conjugated with an enhancing moiety, as detailed above, and the monoclonal antibody-MAG$_2$-GABA-enhancing moiety conjugate is then post-labeled with $^{188}$Re.

B. Peptide Conjugation to a Targeting Protein Prior to Chelation for Radiolabeling If an anchoring peptide and/or peptide-spacer are non-reactive with a chelating agent to be used for radiolabeling, the peptide or spacer moiety may be conjugated to a targeting protein prior to attachment of the chelator.

For instance, succinimidyl 4-(p-maleimidophenyl) butyrate (SMPB) is conjugated to a purified anchoring peptide lacking lysine residues, according to the procedure described in Example I. The SMPB-derivatized anchoring peptide is then reacted with free sulfhydryl groups provided on melanocyte stimulating hormone according to the procedure of Example II.A.

The anchoring peptide-targeting protein conjugate is then reacted with $^{188}$Re-$N_2S_2$-TFP active ester complex, as described in Example II.A. The melanocyte stimulating hormone-anchoring peptide-188Re-MAG-GABA complex may be purified prior to in vivo administration.

EXAMPLE III

Preparation of an Organic Membrane Intercalator-Targeting Protein Conjugate CLC

A. Synthesis of Active Ester of Myristic Acid

An active ester form of myristic acid is obtained through a dicyclohexylcarbodiimide (DCC)-mediated condensation of myristic acid and sulfo-N-hydroxysuccinimide (sulfo-NHS) in a dimethyl-formamide (DMF) solution. To 0.44 ml of DMF is added 0.05 g (0.22 mmole) myristic acid, followed by 0.052 g (0.24 mmole) sulfo-NHS and 0.05 g (0.24 mmole) DCC. Upon addition of DCC, the reaction solution becomes cloudy with the formation of dicyclohexylurea. The reaction mixture is stirred at room temperature for 1 h, and then at −20° C. for 2 h. The reaction mixture is filtered and the solid discarded. The solvent is removed from the filtrate, and the resulting viscous residue is overlaid with methylene chloride. This mixture is stirred overnight at room temperature, and the resultant solid is filtered and dried to obtain the desired active ester of myristic acid (0.09 g) in 97% yield. The active ester product is characterized by thin layer chromatography and nuclear magnetic resonance.

Myristic acid active ester is then conjugated to an antibody F(ab')$_2$ fragment using a 10:1 offering ratio, to provide an average of 1-3 fatty acid molecules per protein conjugate. An active ester form of verrucarin A is then reacted with the antibody F(ab')$_2$ fragment, either before or after chemical linkage of the fatty acid.

EXAMPLE IV

Preparation of a Fusion Protein (Toxin-Enhancing Moiety) - Targeting Protein CLC A ricin A chain-translocating peptide-anchoring peptide fusion protein is produced through recombinant DNA technology. Briefly, the C-terminus of a DNA sequence encoding ricin A chain is ligated by conventional procedures (e.g., using T$_4$ DNA ligase) to a DNA sequence corresponding to a GGG spacer. The C-terminus of the ricin A-GGG DNA sequence is then fused to the N-terminus of a DNA sequence encoding the translocating peptide KGEAALA(EALA)-4EALEALAA.

The N-terminus of a DNA sequence encoding the anchoring peptide AVGAIGAMFLGFLGAAGST-MGAASLC-cys is ligated to a DNA sequence corresponding to a GGG spacer; the N-terminus of the GGG spacer-anchoring peptide-cys DNA sequence is then ligated to the C-terminus of the ricin A-GGG spacer-translocating peptide DNA sequence. The resultant fusion product is diagrammed below.

<u>Ricin A chain</u>—GGG—<u>KGEAALA(EALA)4EALEALAA</u>— ...
   toxin                      translocating ... —GGG—<u>AVGAIGAMFLGFLGAAGSTMGAASL</u>—C
                     anchoring Alternatively, peptide-spacer DNA sequences may be synthesized in vitro using standard oligonucleotide synthesis procedures (see, e.g., U.S. Pat. Nos. 4,500,707 and 4,668,777).

The recombinant ricin A-translocating peptide-anchoring peptide-cys DNA sequence is cloned in an *E. coli* expression vector using conventional procedures. *E. coli* strain HB101 is transformed with the fused recombinant DNA sequence and cultured to produce the ricin A-translocating peptide-anchoring peptide-cys fusion protein. The fusion protein is purified from the transformed *E. coli* culture by standard methods, such as anti-ricin A affinity chromatography or reactive blue 2-sepharose chromatography. The fusion protein may be eluted from the affinity matrix using standard techniques, such as high salt, chaotropic agents, or high or low pH.

The ricin A-translocating peptide-anchoring peptide-cys fusion protein is combined with DTT-treated monoclonal antibody according to the procedure of Example I, in order to obtain a ricir A-translocating peptide-anchoring peptide-monoclonal antibody CLC. The incorporation of both a translocating peptide and an anchoring peptide into the toxin immunoconjugate CLC provides increased cellular membrane interaction, and may provide a corresponding increase in internalization and translocation of the CLC.

EXAMPLE V

Preparation of an Accessory Peptide-Enhancing Moiety-Targeting Protein Conjugate CLC A translocating peptide having an accessory peptide attached at its C terminus may be chemically constructed in a single synthetic process. Briefly, a "translocating-accessory peptide" enhancing moiety composed of the translocating peptide CGEAALA(EALA)4EALEALAA and the casein kinase II substrate accessory peptide AAAAAASEEE is synthesized according to the procedure in Example I. The resultant translocating-accessory peptide is depicted below.

CGEAALA(EALA)-
4EALEALAAAAAAASEEE-amide

The translocating-accessory peptide enhancing moiety may be either: (1) directly attached through its N terminal cysteine to free sulfhydryls present on a DTT-treated targeting protein; (2) attached to a targeting protein by means of a heterobifunctional crosslinker, such as SPDP (see Example I); or (3) attached to a targeting protein via a spacer peptide. The translocating-accessory peptide-targeting protein conjugate is then covalently linked to a trichothecene according to methodology described in U.S. Pat. No. 4,744,981.

Upon in vivo administration of the translocating-accessory peptide-targeting protein-trichothecene CLC, the targeting protein component binds to an appropriate binding site on a target cell. After initial binding and internalization of the targeting protein component, the translocating peptide component of the conjugate traverses the target cell endosomic membrane, causing the accessory peptide component to protrude into the cytoplasm of the target cell. The C terminal 10-mer of the accessory peptide serves as a substrate for the intracellular enzyme casein kinase II, and the serine residue of the 10-mer becomes available for phosphorylation.

Another synthetic translocating-accessory peptide is represented by the following amino acid sequence:

CGEAALA(EALA)4EALEALAADV-
VDADEYLIPQ-amide

The C terminus of the accessory peptide portion of this synthetic peptide serves as a substrate for tyrosine kinase.

Yet another synthetic translocating-accessory peptide contains a spacer region CDNDNDDNDDGGG at the N terminus. A synthetic peptide having an N terminal spacer is illustrated below.

CDNDNDDNDDGGGCGEAALA(EALA)-
4EALEALAAFSLAR-amide

Synthetic peptides of this length may be obtained using an Applied Biosystems 430 A peptide synthesizer, following the manufacturer's N-methylpyrrolidone-DMSO coupling procedure. Alternatively, a spacer-translocating-accessory peptide enhancing moiety may be synthesized using manual solid phase methcdology, as described in Example I. With manual solid phase synthesis, it is preferred that the coupling of all amino acid residues after amino acid 20 is quantitatively monitored by ninhydrin methodology (V. Sarin et al., *Anal. Biochem.* 117: 147–57, 1981). If coupling is less than 99.0% complete at any step, the suboptimally coupled amino acid preferably is coupled a second time, or until coupling is greater than 99.0% complete.

Because longer synthetic peptides may be somewhat heterogeneous, additional purification beyond reverse phase HPLC chromatography, as described in Example I, may be required. For instance, HPLC-ion exchange protocols (F. Regnier, *Meth. Enzymol.* 91: 137, 1983) or hydrophobic interaction chromatography may be used for further purification of heterogeneous synthetic peptides.

An anchoring-accessory peptide enhancing moiety may be synthesized according to the following scheme:

tyr-accessorypeptide-GGG-anchoringpeptide-GGG-cys

The N terminal tyrosine serves as a substrate for tyrosine kinase of H-ras, which is present on the cytoplasmic side of plasma membranes of transformed cells.

A translocating-accessory peptide or an anchoringaccessory peptide enhancing moiety may be conjugated to an targeting protein conjugate according to the procedures described in Examples I and II.

EXAMPLE VI

Assessment of Enhanced Cellular Retention and Translocation of CLCs

Covalently-linked complexes according to Example II or Example IV are assayed for cellular retention by radiolabeling the CLC according to the procedure detailed in Example II, or by any standard radiolabeling methods known in the art. Aliquots of CLC (2–6 ng of targeting protein) are added to $1 \times 10^6$ binding site-positive target cells in 200 μl Dulbecco's minimal essential medium (DMEM) containing 5% fetal bovine serum (FBS). The CLC-target cell mixture is incubated for 1-2 h at 4° C. Following two washes with DMEM, the target cells are resuspended in 200 μl of DMEM-FBS medium and incubated for various periods of time (up to 24 h) at 37° C. Replicate samples are removed at specified time periods and assayed for cell-associated radiolabeled CLC. The assay procedure involves layering the removed cell samples over 1 ml dibutyl- or dinitrophthalate oils, followed by centrifugation at 200×g for 10 min. The centrifuge tubes are cut in half, and the radioactivity associated with the cell pellet is determined. CLCs will demonstrate enhanced retention of cell-associated radioactivity over time as compared to the corresponding unmodified conjugate.

Enhanced in vivo retention of CLCs is determined using nude mouse xenografts of human tumor tissue. A radiolabeled CLC according to Example II or IV that is directed against colon tumor cells is administered intravenously to nude mice xenografted with human colon tumor cells (LS-180). The mice are sacrificed at a various times post-administration, and organs are removed and assayed for radioactivity. CLCs will show prolonged retention in tumor tissue as compared to unmodified conjugates.

Enhanced translocation of toxin-containing CLCs (Examples I and V) is assayed by the following procedure. Toxin activity is determined by means of cytotoxicity tests using the mitochondrial dye 3-(4,5-dimethylthiazol-2-yl)-2,5-diphenyl-2-H-tetrazolium bromide (MTT; Sigma) (T. Mosmann, *J. Immunol. Meth.* 65: 55 (1983)), or by measuring inhibition of $^3$H-leucine incorporation into protein. Toxin CLCs will demonstrate increased potency as compared to unmodified toxin conjugates.

Alternatively, toxin-CLCs are radiolabeled according to standard procedures, and cell-associated/internalized radioactivity determined as described above. By this procedure, the amount of radiolabel on the cell surface or within target cells may be determined. Briefly, aliquots of cells having bound radiolabeled conjugates are incubated with trypsin in sufficient amounts to remove cell surface antigen-antibody complexes. Any remaining cell-associated radiolabel (insensitive to trypsin) has been internalized. Toxin- or drug-CLCs will demonstrate an increase in internalized radiolabel as compared to corresponding radiolabeled unmodified conjugates.

As a direct measure of translocation, conjugates are tested in a translocation assay for pH-dependent membrane binding. For comparison of an unmodified ribosomal inactivating protein (RIP) and a translocating peptide-RIP, samples are incubated in test tubes containing an appropriate volume of 1 mM glycine buffer, pH 5.0 for 30 min at 37° C. These conditions mimic the environment within a target cell endosome. Target cells are resuspended in the same buffer, added to the toxin or translocating peptide-toxin samples, and incubated at 37° C. for 5 min. The cell suspensions are brought to neutrality with 0.1 M Tris, pH 8.0, and cytotoxicity is measured following a further incubation of 48 h. Positive controls include diphtheria toxin, which is known to possess pH-dependent translocating activity, and incubation at pH 7.0 rather than pH 5.0. In a similar manner, targeting protein conjugates containing toxins or modified toxins may be assayed.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for enhancing in vivo cytotoxicity of a targeting protein conjugate comprising administering to a tumor-bearing patient a therapeutically effective amount of a covalently-linked complex (CLC) comprising a targeting protein or a targeting peptide; a cytotoxic agent; and an enhancing moiety capable of promoting CLC-membrane interaction, wherein the enhancing moiety exhibits alpha helical structure at acidic pH and substantially unfolds at physiological pH and exhibits little or no tertiary structure.

2. The method of claim 1 wherein the targeting protein or targeting peptide is an antibody, an antibody fragment or an antigen-binding portion of an antibody.

3. The method of claim 1 wherein the cytotoxic agent is a radionuclide; a toxin or a fragment or analog thereof; a drug or an analog thereof; or a combination of the foregoing.

4. The method of claim 3 wherein the radionuclide is selected from the group consisting of $^{188}$Re, $^{186}$Re, $^{203}$Pb, $^{212}$Pb, $^{67}$Cu, $^{90}$Y, $^{125}$I, $^{131}$I, $^{77}$Br, $^{211}$At, $^{97}$Ru, $^{105}$Rh, $^{198}$Au, $^{199}$Au and $^{119}$Sb.

5. The method of claim 1 wherein the enhancing moiety is a translocating peptide, an anchoring peptide, an organic membrane intercalator or a combination thereof.

6. A method of claim 1 wherein the targeting protein or targeting peptide comprises a synthetic protein or synthetic peptide.

7. A method of claim 1 wherein the targeting protein or targeting peptide comprises an analog of an antibody, an antibody fragment or an antigen-binding portion of an anitbody that retains the capacity to bind to a defined target cell population.

8. A method for enhanced in vivo imaging of a tumor comprising administering to a tumor-bearing patient a diagnostically effective amount of a covalently-linked complex (CLC) comprising a targeting protein or a targeting peptide; a radionuclide selected from the group consisting of gamma-emitters, positron emitters and X-ray emitters; and an enhancing moiety capable of promoting CLC-membrane interaction, wherein the enhancing moiety exhibits alpha helical structure at acidic pH and substantially unfolds at physiological pH and exhibits littel or no tertiary structure.

9. The method of claim 8 wherein the targeting protein or targeting peptide is an antibody, an antibody fragment or an antigen-binding portion of an antibody.

10. The method of claim 8 wherein the radionuclide is selected from the group consisting of $^{188}$Re, $^{186}$Re, $^{67}$Cu, $^{131}$I, $^{97}$Ru, $^{105}$Rh, $^{123}$I, $^{111}$In, $^{67}$Ga, $^{99m}$Tc and $^{18}$F.

11. The method of claim 8 wherein the enhancing moiety is a translocating peptide, an anchoring peptide, an organic membrane intercalator or a combination thereof.

12. A method of claim 8 wherein the targeting protein or targeting peptide comprises a synthetic protein or a synthetic peptide.

13. A method of claim 8 wherein the targeting protein or targeting peptide comprises an analog of an antibody, an antibody fragment or an antigen-binding portion of an antibody that retains the capacity to bind to a defined target all population.

* * * * *